United States Patent [19]
Haaga

[11] Patent Number: 5,477,862
[45] Date of Patent: Dec. 26, 1995

[54] CUTTING TIP FOR BIOPSY NEEDLE

[76] Inventor: John R. Haaga, 4309 N, Hilltop, Chagrin Falls, Ohio 44022

[21] Appl. No.: 209,890

[22] Filed: Mar. 14, 1994

[51] Int. Cl.⁶ ............................................. A61B 10/00
[52] U.S. Cl. .................................................... 128/754
[58] Field of Search ........................ 128/749, 751–755, 128/757, 758; 606/167, 185

[56] References Cited

U.S. PATENT DOCUMENTS

| | | | |
|---|---|---|---|
| 737,293 | 8/1903 | Summerfeldt | 128/751 |
| 2,603,217 | 11/1949 | McShirley | 128/239 |
| 2,691,373 | 11/1951 | Bried | 128/239 |
| 2,814,296 | 4/1955 | Everett | 128/339 |
| 2,919,692 | 1/1960 | Ackermann | 128/754 |
| 3,106,483 | 11/1963 | Kline | 117/62.2 |
| 3,358,684 | 12/1967 | Marshall | 128/214.4 |
| 3,396,727 | 8/1968 | Mount | 128/349 |
| 3,477,423 | 11/1969 | Griffith | 128/2 |
| 3,530,860 | 9/1970 | Majoros | 128/305 |
| 3,736,939 | 6/1973 | Taylor | 128/349 |
| 3,888,258 | 6/1975 | Akiyama | 128/305 |
| 4,306,563 | 12/1981 | Iwatschenko | 128/349 |
| 4,340,066 | 7/1982 | Shah | 128/749 |
| 4,396,021 | 8/1983 | Baumgartner | 128/754 |
| 4,564,361 | 1/1986 | Akiyama | 604/265 |
| 4,600,014 | 7/1986 | Beraha | 128/754 |
| 4,646,739 | 3/1987 | Doyle | 128/325 |
| 4,650,488 | 3/1987 | Bays et al. | 623/12 |
| 4,702,261 | 10/1987 | Cornell et al. | 128/754 |
| 4,708,147 | 11/1987 | Haaga | 128/753 |
| 4,710,181 | 12/1987 | Fuqua | 604/280 |
| 4,735,215 | 4/1988 | Goto | 128/754 |
| 4,827,940 | 5/1989 | Mayer | 128/642 |
| 4,838,280 | 6/1989 | Haaga | 128/751 |
| 4,936,835 | 6/1990 | Haaga | 604/265 |
| 4,953,558 | 9/1990 | Akerfeldt | 128/751 |
| 5,057,082 | 10/1991 | Burchette | 606/167 |
| 5,061,281 | 10/1991 | Mades et al. | 623/11 |
| 5,080,655 | 1/1992 | Haaga | 604/265 |
| 5,195,988 | 3/1993 | Haaga | 604/265 |
| 5,224,951 | 7/1993 | Freitos | 128/754 |
| 5,254,105 | 11/1993 | Haaga | 604/265 |
| 5,273,051 | 12/1993 | Wilk | 128/751 |
| 5,318,580 | 6/1994 | Gresl | 606/185 |

FOREIGN PATENT DOCUMENTS

| | | |
|---|---|---|
| 0019104 | 11/1980 | European Pat. Off. . |
| 8623592 | 11/1987 | Germany . |
| 3632197 | 3/1988 | Germany . |
| 728852 | 5/1980 | U.S.S.R. . |
| 8201988 | 6/1982 | WIPO . |

OTHER PUBLICATIONS

Becton et al. "Bigsy Needles & Instruments For Advanced Techniques" Oct. 1974.

*Primary Examiner*—Max Hindenburg
*Attorney, Agent, or Firm*—Vickers, Daniels & Young

[57] ABSTRACT

An improved, cone shaped puncturing/cutting tip is provided for the inner cannula or alternative, the stylet, of a biopsy needle. The cone shaped tip is defined by a frontal vertex co-incident with the center of the cannula or the stylet and a circular base of diameter about equal that of the cannula or stylet. The surface of the cone shaped tip end includes at least three circumferentially spaced, longitudinally extending cutting vane edges extending from the vertex to the base and is hollowed between adjacent vane cutting edges whereby cutting penetration of said tip to the site is enhanced without significant vertex deflection of the point during penetration.

28 Claims, 3 Drawing Sheets

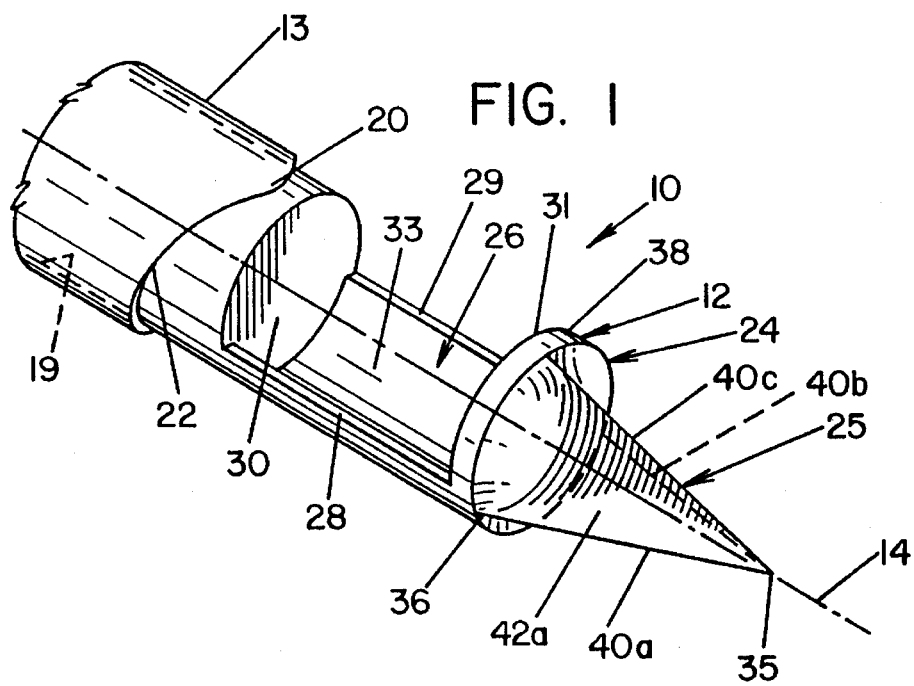
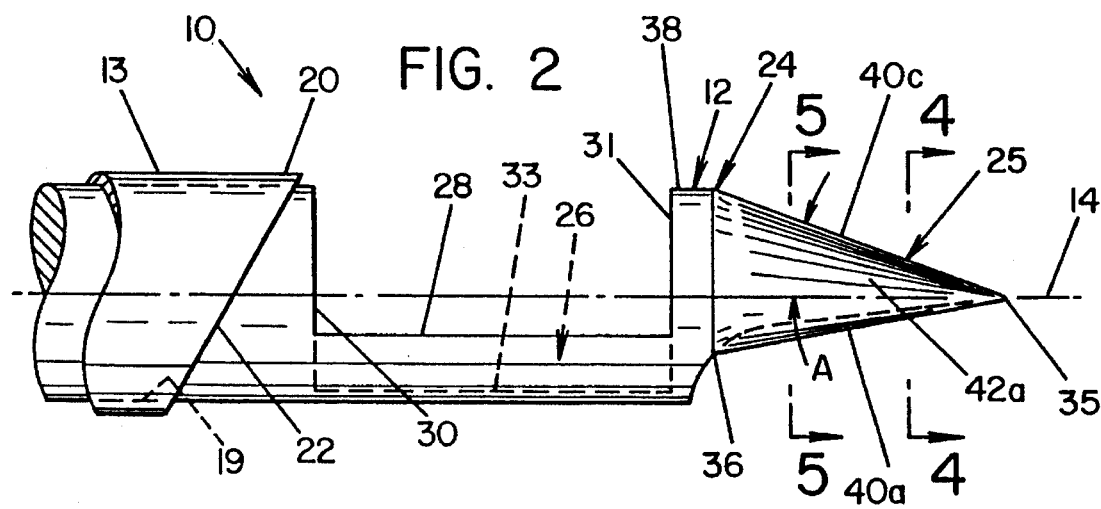
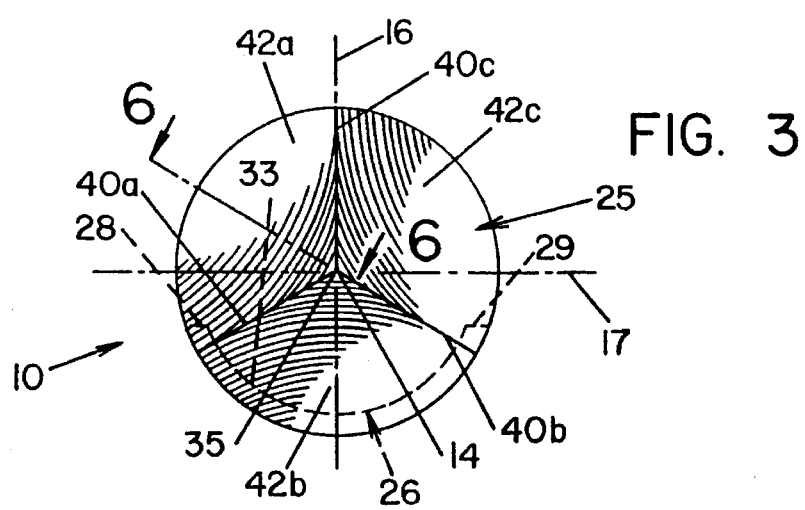

CUTTING TIP FOR BIOPSY NEEDLE

This invention relates generally to surgical needles and more particularly to biopsy needles.

The invention is particularly applicable to biopsy needles, whether of the side or end cut, and will be described with specific reference thereto. However, the invention may have broader application and may be used in any surgical application in which the function of a cutting needle or an aspiration needle is to be performed.

INCORPORATION BY REFERENCE

My prior U.S. Pat. Nos. 4,708,147, dated Nov. 24, 1987 and entitled "Universal Biopsy Needle"; 4,838,280, dated Jun. 13, 1989 and entitled "Hemostatic Sheath for a Biopsy Needle and Methods of Use" and 5,080,655 dated Jan. 14, 1992 and entitled "Medical Biopsy Needle" are incorporated by reference herein so that needle structure, details and the like disclosed in those patents need not be discussed in detail herein. My prior patents do not form a part of the present invention.

BACKGROUND

Biopsy needles are generally classified as being either an end cutting needle, commonly referred to as a "Menghini needle" or, a side cutting needle such as the type generally known as "Tru-cut" needles. The present invention was specifically developed as an improvement to the Tru-cut needle, but, as discussed hereafter, can also be used as an end cutting needle.

Generally, an end cutting needle includes a hollow cannula having an especially configured, circumferentially sharpened, open end at its distal portion. A stylet is conventionally inserted into the hollow shaft of the cannula and extends flush with the open cutting edge of the cannula to close the open end. The biopsy needle is then inserted and the stylet functions to puncture the site of the lesion where the biopsy specimen is to be taken. The stylet is then withdrawn and the cannula further inserted into the lesion with the result that the tissue is cut and fills the now open cutting end of the cannula. A suction device is typically applied to a proximal portion of the cannula to withdraw the tissue sample thus taken. Alternatively, the cannula can be rotated to sever the tissue and then withdrawn from the site. Reference should be had to my '147 patent and particularly FIGS. 7–13 thereof which show prior art, end cut needles.

In the side cut needle, there is a "solid" inner cannula within an outer cannula and the inner cannula generally has a leveled, circumferentially sharpened distal end shaped to a pointed end with a cutting groove or tissue gap formed at the distal portion of the inner cannula behind the pointed end. The side cut needle advances to the site where the lesion is to be extracted and is rotated so that the cutting groove severs the tissue. The outer cannula advances over the inner cannula to encapsulate the specimen there between. Alternatively, the outer cannula can have a cutting edge formed about its opening and simply be advanced over the tissue gap space to cut the lesion or biopsy specimen thus trapping the specimen within the gap.

The most widely used cutting and puncturing tip of a biopsy needle is simply that of a beveled tip which is circumferentially and axially sharpened to a point. The bevel lies in a plane which forms an acute angel with the longitudinal center line of the cannula, typically anywhere from 20° to 45°. Conical pointed ends have also been used to puncture the site. (See for example FIG. 4a and FIG. 11 of my '174 patent.) Technically, conical pointed needle tips do not cut the tissue nor do they have a mechanism to prevent deviation. They merely puncture the site. The circumferentially sharpened end of the cannula is used to cut the lesion.

As noted in my prior patents, complications can arise from the use of biopsy needles while positioning the needle and while severing the specimens to be taken. To accurately guide the biopsy needle, percutaneous procedures have been developed which permit visual radiological observation of the instrument inside the body. In fact, biopsy needles have been developed with a configuration to provide good images in conjunction with CT guided biopsies. Also, better CT scanning images have been developed as the scanning art has advanced which enable the entire distal portion of the needle to be accurately positioned within the site where the biopsy specimen is to be extracted.

Nevertheless, it should be understood that the characteristics of lesion tissue vary and in some instances may be determinable only during the biopsy procedure. While some tissue is resilient, other tissue may be hard and resistant to penetration. Specifically in biopsies of the breast, the tumors or lesions are often small, hard masses. When the needle tries to penetrate or puncture the tumor, the needle tip will actually deflect before the tumor is punctured. Often the tumor will move when the needle tip deflects making extraction of the specimen difficult or impossible. Sometimes fracture of the tumor will occur when the needle deflects causing complications.

Conceptually, there are other procedures where body organs or parts, even bone, have to be accessed to withdraw a specimen by penetrating rigid matter. In these "hard applications" in which access is to be provided by a needle, the needle tip, especially the beveled tip (but also the cone shaped tip) deflects during the puncture/cutting/insertion portion of the procedure. The deflection prevents accurate positioning of the needle.

SUMMARY OF THE INVENTION

Accordingly, it is a principle object of the invention to provide a needle for biopsy sampling purposes and the like which has a central point cutting end that not only resists deflection but also enhances the cutting of the lesion during puncture thus permitting accurate positioning of the needle and withdrawal of the biopsy specimen at the puncture site.

This object along with other features of the invention is achieved in a biopsy needle which includes a first longitudinally extending cylindrical member having a proximal and a solid, cone shaped distal puncturing and cutting end. The cone shaped end is defined by a frontal vertex coincident with the center of the first cylindrical member and a circular base of diameter about that of the first member. The cone shaped puncturing and cutting end has a surface which includes a plurality of circumferentially spaced, longitudinally extending cutting vane edges each of which extends from the vertex to the base and the surface of the cone shaped end is hollowed between adjacent vane edges whereby cutting penetration of the distal end to the biopsy site is enhanced without significant vertex deflection. A second cylindrical member associated with the first member is provided for withdrawing the biopsy specimen from the site.

In accordance with other specific features of the invention, the vane edges which preferably number three are spaced in equal circumferentially spaced increments about the distal end and the vane edges lie in a plane forming an acute angle with the longitudinal axis of the needle within the range of about 20° to about 75°, and preferably, within the range of about 20° to about 45°, to provide a geometric arrangement which rigidizes the needle point thus assuring accurate positioning of the needle during puncture of small lesions.

In accordance with another specific feature of the invention the surface of the distal cutting end is hollowed in a concave direction between adjacent vane cutting edges and more specifically the distal end has a cross-sectional configuration in which the surface between adjacent cutting vane edges is arcuate whereby the vane cutting edges can be ground razor sharp in a rigid manner permitting the pointed vertex to enter into hard lesions by actually cutting the needle's path into the lesion thereby minimizing the puncture force of the needle which otherwise would tend to displace or fracture the tumor or lesion. Furthermore, and importantly, the vanes act to stabilize the direction of the needle during movement, similar to stabilizers on a rocket or arrow.

In accordance with another aspect of the invention the needle's first member is a solid inner cannula which has a recess or pocket adjacent the distal cone shaped end. The recess has first and second circumferentially spaced, longitudinally extending cutting edges defining a tissue gap into which the specimen is retained whereby the biopsy needle functions as a side cut needle. Alternatively, the first member comprises a stylet and the second member comprises a hollow cylindrical cannula having a circumferentially sharpened distal end through which the distal end of the stylet protrudes whereby the biopsy needle functions as an end cut needle. The invention is thus applicable to both side and end cut biopsy needles.

It is thus another object of the invention to provide an improved biopsy needle utilizing an especially configured somewhat cone shaped pointed end which not only permits the needle to puncture the biopsy site but also permits the biopsy needle to cut into the site as the needle punctures the site thus enhancing accurate penetration and positioning of the needle at the biopsy site.

It is another object of the invention to provide a special biopsy needle tip comprising a plurality of cutting vanes longitudinally extending from a circular base and converging to a centered point for cutting into hardened lesions with improved directional stability.

It is yet another object of the invention to provide a strengthened puncturing end for a biopsy needle.

It is still yet another object of the invention to provide an improved biopsy needle for performing breast biopsies.

It is yet another object of the invention to provide an improved penetrating/cutting distal end for a biopsy needle which utilizes a razor sharp skid configuration to permit penetration of hardened lesions and tumors with less force than what was heretofore required.

It is still another object of the invention to provide an improved biopsy cutting tip which is especially adapted to puncturing, penetrating and cutting biopsy samples from relatively small, hard lesion masses.

A still further object of the invention is to provide an improved puncturing, cutting tip for both side and end cut biopsy needles and small catheters for fluid or air draining.

Further objects and advantages of the invention will become apparent to those skilled in the art from reading and understanding the following detailed description of the species thereof and from the accompanying drawings which illustrate preferred embodiments that the invention may take in physical form and in certain parts and arrangement of parts.

BRIEF DESCRIPTION OF THE DRAWINGS

FIG. 1 is a perspective view of a portion of a biopsy needle employing the improved needle tip of the present invention;

FIG. 2 is a side elevation view of the needle illustrated in FIG. 1;

FIG. 3 is an end view of the needle tip of the present invention;

DETAILED DESCRIPTION OF THE INVENTION

Figure 5:
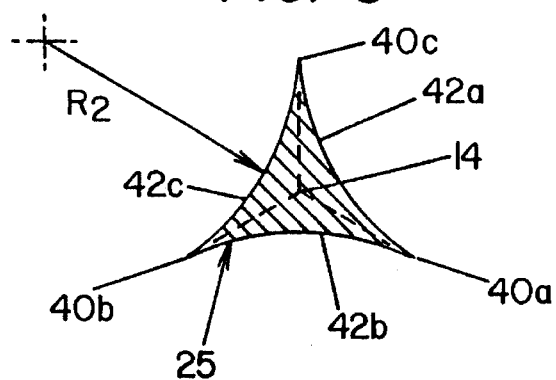
FIGS. 4 and 5 are cross-sectional, transverse views of the needle tip of the present invention taken along lines 4—4 and 5—5 respectively of FIG. 2.

Referring now to the drawings wherein the showings are for the purpose of illustrating preferred embodiments of the invention only and not for the purpose of limiting the same, there is shown in FIG. 1 a biopsy needle 10 of the side cut type. Biopsy needle 10 includes a first cylindrical member 12 which, for the side cut biopsy needle 10 shown in FIG. 1, is a "solid", elongated, cylindrical inner cannula. Inner cannula 12 is slidingly received within a hollowed, elongated, cylindrical second member which for the biopsy needle shown in FIG. 1 is an outer cannula 13. Both inner and outer cannulas 12, 13 axially extend along and are concentric with longitudinal center line 14 of biopsy needle 10. For purposes of future reference, biopsy needle 10 may be described with reference to a vertical plane 16 coincident with longitudinal center line 14 and a horizontal plane 17 also coincident with longitudinal center line 14. The direction along the axial length of biopsy needle 10 is referred to as longitudinal. The direction of cross-sectional planes through biopsy needle 10 will be referred to as transverse.

Elongated outer cannula 13 has a cylindrical passageway 19 which, as noted, slidingly receives inner cannula 12 and a distal end 20 and a proximal end, not fully shown, which may be of any suitable design adapted for the type of biopsy being performed. For example, when an end cut biopsy needle 10 is used, a conventional suctional device will be attached to the proximal end to assure retention of the specimen, etc. Distal end 20 has a distal cutting edge 22 which is circumferentially and axially sharpened or ground to permit outer cannula 13 to slide forward relative to inner cannula 12 to assure severance of the lesion. Outer cannula 13 is conventional.

Figure 7:
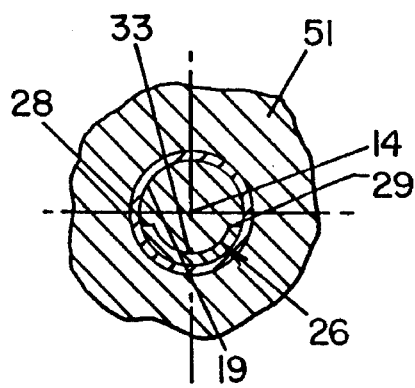
FIG. 7 is a cross-sectional view of the biopsy needle illustrating encapsulation of the biopsy specimen therein.

Inner cannula 12 has a distal portion 24 and an elongated, cylindrical proximal portion, not completely shown, which is slidingly received within cylindrical passageway 19 of outer cannula 13 as noted. Distal portion 24 includes a somewhat cone shaped puncturing/cutting end which will simply be hereafter referred as cone shaped tip 25 and a recess or pocket 26, defining a tissue gap, extending rearwardly from the base of cone shaped tip 25. As best shown in FIGS. 1, 2 and 7, recess 26 is defined by two longitudinally extending cutting edges 28, 29 which are contiguous with and in between a circular rearward base surface 30 and a circular forward base surface 31 each of which lie in a plane parallel to vertical plane 16. As best shown in FIG. 7, recess cutting edges 28, 29 are also contiguous with a cylindrical, transversely extending inner surface 33. Recess 26 is conventional and defines the tissue gap in a side cut biopsy needle containing the biopsy specimen. As is well known, when inner canula 12 is positioned at the site of the biopsy, inner cannula 12 is simply rotated to permit cutting edges 28, 29 to sever the specimen which is retained by forward relative motion of outer cannula 13 to encapsulate or retain the specimen within pocket recess 26. Alternatively, with inner cannula 12 positioned at the site, outer cannula 13 can be slid forward with outer cannula cutting edge 22 severing the specimen for retention in the tissue gap.

Referring now to FIGS. 1–6, cone shaped tip 25 of inner cannula 12 has a vertex 35 or point coincident with longitudinal center line 14 and a base 36 of diameter approximately equal but preferably not greater than the diameter of inner cannula 12. Base 36 can be contiguous with circular forward base surface 31 of pocket recess 26 or, as shown in FIG. 2, base 36 can be contiguous with a cylindrical spacer surface 38, which, in turn, terminates at circular forward base surface 31. Unlike other cone shaped needle tips, the surface of cone shaped tip 25 is defined by a plurality of circumferentially spaced, vane cutting edges 40 each of which extends, in a generally longitudinal direction, from vertex 35 to cone base 36 or to a position adjacent cone base 36. Three vane cutting edges 40 are shown and designated by reference numerals 40a, 40b and 40c in FIG. 3. In accordance with the broad inventive concept, any number of cutting vane edges greater than three can be used, but the triangular arrangement of vane cutting edges 40 is definitely preferred over other configurations. Each cutting vane edge 40 lies in a plane which passes through longitudinal center line 14 and which forms an acute angle with longitudinal center line, designated by reference letter "A" in FIG. 2, which can vary anywhere from about 20 to 70 degrees and preferably is between about 20 to 45 degrees. This angular range has been found to be preferred in my '147 patent and is believed likewise applicable to this invention.

The surface of cone shaped tip 25 between adjacent vane edges, 40a–b, 40b–c, 40a–c, is hollowed and is designated by reference numeral 42, there being three such hollowed surfaces designated 42a, 42b and 42c. In accordance with the broad inventive concept, any hollowed configuration can be employed so long as the configuration of each hollowed surface, 42a, 42b, 42c is generally symmetrical and identical to one another. More specifically, in accordance with the broad inventive concept, hollowed surfaces 42a, 42b and 42c could simply be flat, straight line surfaces, each of which extends from vertex 35 but may not necessarily extend all the way to cone base 36. Obviously, if hollowed surfaces 42 do not extend to cone base 36, vane cutting edges 40 simply merge or blend into the conical surface and cease to exist. (However, for definitional purposes, cone base 36 would then lie in a plane parallel to vertical plane 16 whereat vane cutting edges 40 and hollowed surfaces 42 cease to exist. This occurs in the preferred embodiment shown in the drawings at the surface designated by reference numeral 36.)

Figure 4:
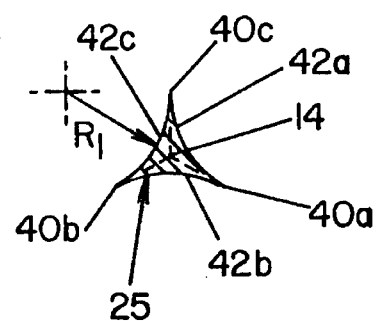
Figure 6:
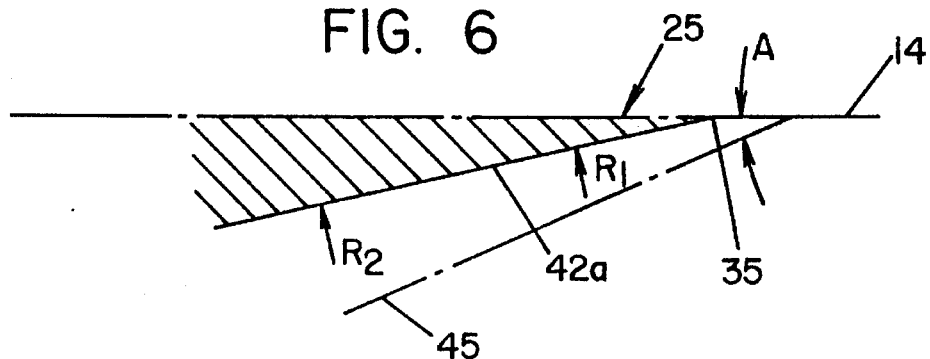
FIG. 6 is a sectioned view of the needle tip of the present invention taken along lines 6—6 of FIG. 3.

It is however preferred, and a specific concept of the invention, that hollowed surface 42 be hollowed or scalloped in a generally concave direction. One configuration is shown in FIGS. 4–6 although other concave surface shapes will suggest themselves to those skilled in the art. Hollowed surface 42 is shown as being arcuate and more specifically is defined as an arcuate surface struck from a single arc having a radius designated as R-1 (although hollowed surface 42 could be in a curvalinear form defined by a plurality of arcs blending into one another). The radius varies depending on the axial position of the radius relative to vertex 35 and cone base 36 so that the radius is larger adjacent cone base 36 and smaller adjacent vertex 35. Thus arcuate surface has a larger radius, designated R-2 in FIG. 5 than that of hollowed surface 42 designated by an arc having radius R-1 shown in FIG. 4. For the hollowed surface 42 shown in FIGS. 4 and 5, the center of the arcs defining hollowed surface 42 lie on a common arc axis designated by reference number 45 in FIG. 6 which intersects longitudinal center line 14 and preferably forms an acute angle with longitudinal center line 14. For symmetrical purposes the acute angle formed by arc axis 45 is equal to the angle shown as angle "A" in FIG. 2.

The length of the radius defining hollowed surfaces 42 must be sufficiently great so that the intersection of adjacent hollowed surfaces 42a–b, 42b–c, 42a–c, form a sharp point and those points or loci of points form a line which defines cutting vane edges 40a, 40b, and 40c. This configuration allows or permits cutting vane edges 40 to be ground razor sharp. Further the depth of the hollowed surface 42 permits some flexure of cutting vane edges 40 while needle tip is inserted into the hard lesion and at the same time the triangular orientation of the cutting vane edges 40 retains rigidity of cone shaped tip 25 and particularly maintains vertex 35 in its centered position with minimal deflection during needle puncture.

Figure 8:
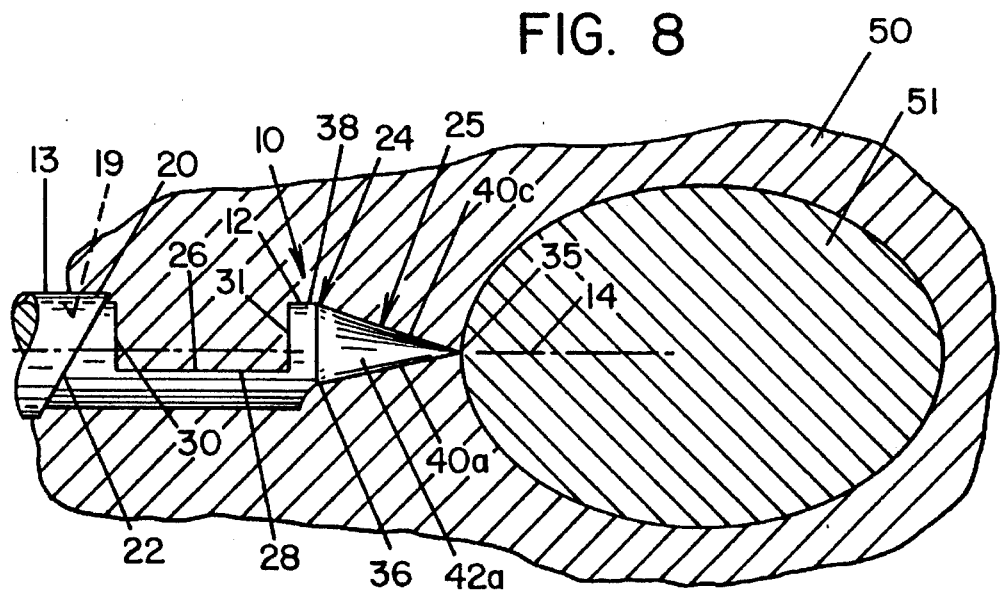
FIGS. 8 and 9 generally illustrate the initial insertion of the needle of the present invention into a lesion whereat the biopsy specimen is taken.
Figure 9:
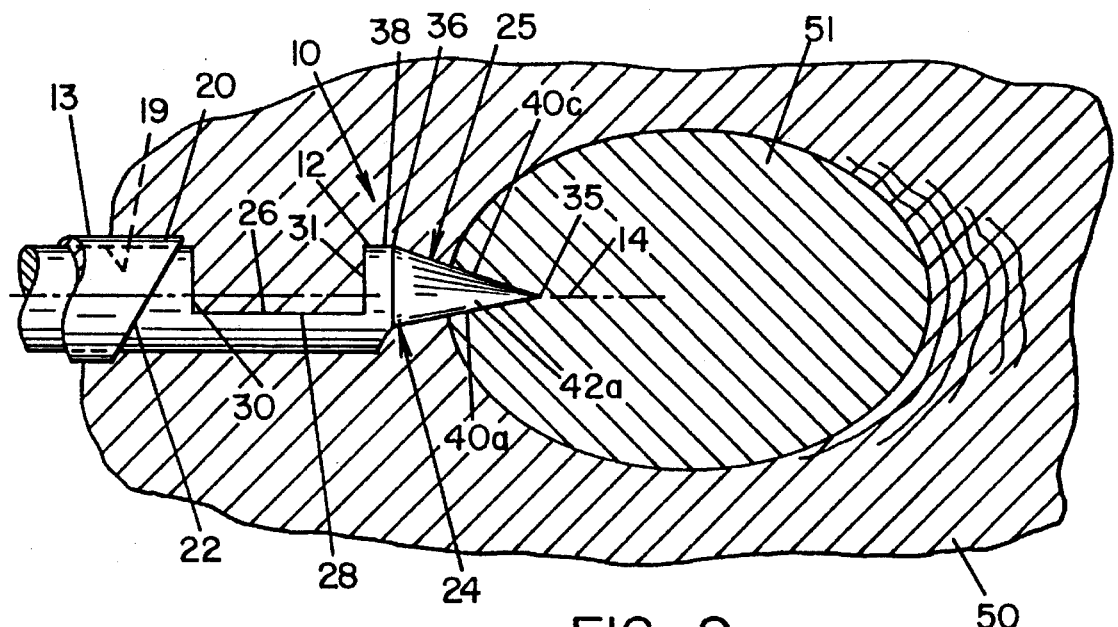

This is diagrammatically illustrated in FIGS. 8 and 9 in which needle 10 is shown as having already penetrated tissue 50 and is being moved into contact with a small, hardened lesion or tumor 51 which may be encountered in a breast biopsy. Vertex 35 initially contacts or sticks tumor 51 and as shown in FIG. 9, when needle 10 is advanced, vertex 35 does not deflect and cutting vane edges 40 slice into tumor 51. The action can be likened to especially configured runners recently used on Olympic toboggans which slice through hard packed snow permitting the toboggan to travel fast. In this instance, the triangular configuration of cutting vane edges 40 coupled with hollowed surfaces 42 permit cone shaped tip 25 to penetrate and cut into hardened tumor 51 with less force than that previously required for Tru-Cut needles with the result that tumor 51 tends to stay in its relative position within tissue 50 as shown in FIG. 9. Breast biopsies can now be taken with less complications. In addition, cutting vane edges 40 provide directional guidance to biopsy needle 10 thus insuring that biopsy needle 10 does not deviate from its intended direction during puncture. In the beveled prior art needles, deflection of the needle top caused directional change of the needles.

Figure 10:
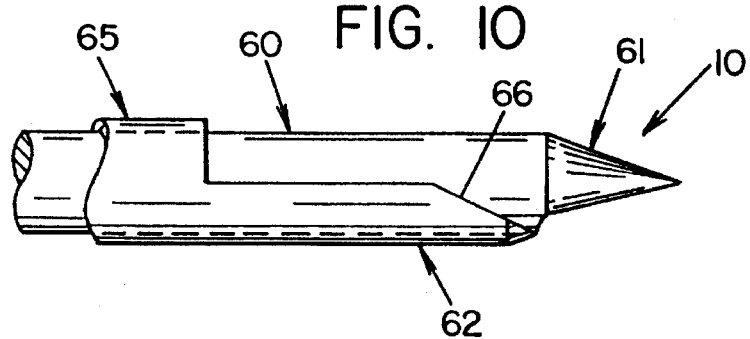
FIG. 10 is an alternative embodiment of the improved needle tip applied to an end cut biopsy needle.

While the invention has particular application to side cut biopsy needles as described above, the invention can also be used for end cut biopsy needles as shown in FIG. 10. Needle 10 in FIG. 10 includes a first cylindrical member or stylet 60 which has a cone shaped distal end 61 identical to cone shaped tip 25 described above and thus not further described herein. Stylet 60, of course, has a solid, elongated cylindrical proximal end (not fully shown) which slides within a hollowed, outer cylindrical end cut cannula 65 having an axially and circumferentially open distal end 66. Outer end cut cannula 62 (or the second cylindrical member of needle 10) is shown having a configuration which is described in detail in my U.S. Pat. No. 4,708,147 and reference can be had to my patent for a description of outer cannula 62 which will not be further described herein. Other designs of conventional outer cannulas used in end cutting biopsy needles can be used. The FIG. 10 needle functions in a conventional manner. Stylet 60 punctures and, unlike other pointed stylets, cuts the lesion and is withdrawn. End cutting outer cannula 65 is then advanced into the lesion (or alternatively, simply rotated to cut the specimen because stylet 60 has advanced needle 10 to the point where the specimen can be taken) and the biopsy specimen severed and removed in conventional manner.

As noted above, cone shaped tip 25 can be viewed as somewhat cone shaped. Alternatively, cone shaped tip 25 could be defined as including a plurality of straight line cutting vane edges 40, each of which extend generally longitudinally from cone base 36 (about which cutting vane edges 40 are circumferentially spaced in equal increments) and converge to vertex 35 at which they intersect one another. Cutting vane edges thus lie on a surface which defines a cone having vertex 35 and base 36. The surface of the cone shaped tip 25 between adjacent cutting vane edges 40 is thus defined as hollowed surface 42 as described above.

Cannulas 12 and 13 are conventionally formed of hardened stainless steel which can be ground sharp for cutting purposes. It is within the scope of this invention that cone shaped tip 25 can be made of hardened gelatin as disclosed in my '655 patent which shows a two-dimensional arrow, gelatin tip hypodermic needle. The hardened gelatin can have vane cutting edges 40 ground sharp and the gelatin will then dissolve at the site as explained in my '655 patent. There could be certain surgical procedures where this type of needle is desired.

The invention has been described with reference to a preferred and alternative embodiment. Obviously modifications and alterations will suggest themselves to those skilled in the art. For example, the invention is applicable to biopsy needles having several cannulas and not just an inner and an outer cannula. As noted above, the invention is applicable to other types of surgical needles which must use a puncturing/cutting tip to gain access to a site, organ etc. It is intended to include all such modifications, alterations and/or applications insofar as they come within the scope of the present invention.

Having thus defined the invention, it is claimed:

1. A biopsy needle of the side or end cut type comprising a first, longitudinally-extending cylindrical member having a proximal end and a solid, somewhat cone shaped distal puncturing and cutting end, said cone shaped end defined by a frontal vertex co-incident with the center of said first cylindrical member and lying on its longitudinally-extending axis, said cone shaped end having a circular base of diameter about that of said first member and having a surface including at least three circumferentially spaced, longitudinally-extending cutting vane edges extending from said vertex to said base, said surface being arcuate in cross-sectional configuration between adjacent vane cutting edges whereby cutting penetration of said distal end to the biopsy site is enhanced without significant vertex deflection and means including a second cylindrical member associated with said first member for withdrawing a specimen from said site.

2. The needle of claim 1 wherein said vane edges are three in number and are spaced in equal circumferential increments about said distal end.

3. The needle of claim 2 wherein each of said vane edges lying in a plane forming a first acute angle with said longitudinal axis.

4. The needle of claim 3 wherein said acute angle is in the range of 20° to 45°.

5. The needle of claim 1 wherein said first member is a cannula, said cannula having an intermediate, hollow section adjacent said distal end, said intermediate section having first and second circumferentially spaced, longitudinally-extending cutting edges defining a tissue gap into which the specimen is retained in said first member.

6. The needle of claim 5 wherein said first member is an inner cannula and said second member is an outer cannula receiving said inner cannula, said inner cannula being rotatable within said outer cannula for severing said specimen from the biopsy site.

7. The needle of claim 1 wherein said first member is a stylet and said second member is a hollow cannula having a distal end, said stylet received within said cannula, and extending beyond said cannula for effecting puncture, said hollow cannula having a cutting edge adjacent its distal end for withdrawing a specimen from the biopsy site.

8. The needle of claim 1 wherein said distal end is made from hardened gelatin for dissolving after puncture.

9. The needle of claim 1 wherein said arcuate surface between adjacent vane edges is defined by an arc struck from an arc axis which intersects said first member's longitudinally-extending axis.

10. The needle of claim 9 wherein each of said vane edges lie in a plane forming an acute angle with said longitudinal axis and said arc axis intersects said longitudinal axis at about the same angle.

11. A biopsy needle for penetrating and removing hard lesions comprising:

a first inner cylindrical cannula having a distal puncturing and cutting end, a proximal end and an intermediate section adjacent said end having a hollowed recess formed by first and second longitudinally-extending cutting edges to define a tissue gap in said inner cannula for receiving a biopsy specimen from the biopsy site, a second hollow cylindrical cannula receiving said first cannula having a distal end and a proximal end, said distal end of said second cannula having a cutting edge formed thereabout; and said distal end of said first cannula being solid and somewhat cone shaped in configuration and having a frontal vertex co-incident with the center of said first cannula and a base of diameter about that of said first cannula, said distal end having a surface including a plurality of circumferentially spaced cutting vane edges extending from said vertex to said base, said surface between adjacent vane edges forming a concave arcuate web defined in cross-sectional configuration by a single arc whose radius lies on an axis which intersects the longitudinal axis of said first cannula.

12. The needle of claim 11 wherein said vane edges are three in number and are spaced in equal circumferential increments about said distal end.

13. The needle of claim 12 wherein each of said vane edges lying in a plane forming a first acute angle with said longitudinal axis.

14. The needle of claim 13 wherein said acute angle is in the range of 20° to 45°.

15. The needle of claim 14 wherein said concave web surface is further defined by an arc struck from an arc axis which intersects said longitudinal axis.

16. A biopsy needle specifically adapted for penetrating relatively small, hard lesions typically found in breast tissue comprising:

a first cylindrical cannula having a distal end and a proximal end, a cylindrical stylet having a distal end and a proximal end received within said first cannula and withdrawn therefrom after puncturing the biopsy site, said distal end being somewhat cone shaped and having a vertex co-incident with the center of said stylet and a base about equal in diameter to that of said stylet, said cone-shaped distal end of said stylet having a plurality of vane cutting edges circumferentially spaced from one another about said distal end and extending from said vertex to said base and the surface of said cone shaped distal end between adjacent vane edges being formed as a concave web surface defined in cross-sectional configuration as arcuate whereby said vane edges are ground razor sharp for ease of penetration to the biopsy site while minimizing deflection of said vertex during penetration to permit accurate positioning of said needle.

17. The needle of claim 16 wherein said vane edges are three in number and are spaced in equal circumferential increments about said distal end.

18. The needle of claim 17 wherein said stylet has a centered, longitudinally-extending axis, each of said vane edges lying in a plane forming a first acute angle with said longitudinal axis.

19. The needle of claim 18 wherein said acute angle is in the range of 20° to 45°.

20. The needle of claim 16 further including a second cylindrical cannula receiving said first cannula, said first cannula having a recessed pocket formed adjacent its distal end for receiving a specimen from the biopsy site.

21. The needle of claim 20 wherein said web surface between adjacent vane edges is defined in cross-sectional configuration by an arc struck from an arc axis which intersects said stylet's longitudinally-extending axis.

22. The needle of claim 21 wherein said arc axis forms an acute angle of about 20° to 45° with said longitudinally-extending axis.

23. In a biopsy needle of the side or end cut type for penetrating and sampling hard lesions having a cannula with a recess for extracting a specimen from the biopsy site and means at the distal end of said needle for puncturing the site, the improvement comprising:

a solid, somewhat cone shaped distal end having a vertex at the center of said cannula lying on the cannula's longitudinal axis and a base of diameter not greater than that of said cannula, said distal end having a plurality of vane cutting edges, each vane longitudinally extending from said vertex to said base and the surface of said distal end between adjacent cutting vanes being arcuate in a concave direction whereby said vertex is strengthened to minimize deflection of said distal end while said cutting edges can be formed razor sharp to ease penetration of said needle into tissue at the biopsy site.

24. The improvement of claim 21 wherein said vane edges are three in number and are spaced in equal circumferential increments about said distal end.

25. The improvement of claim 24 wherein each of said vane edges lying in a plane forming a first acute angle with said longitudinal axis.

26. The improvement of claim 25 wherein said acute angle is in the range of 20° to 45°.

27. The improvement of claim 26 wherein said arcuate surface is defined by an arc struck from an arc axis which intersects said cannula's longitudinal axis.

28. The improvement of claim 27 wherein said arc axis forms an acute angle of about 20° to 45° with said longitudinally-extending axis.

* * * * *